United States Patent

Baker et al.

[11] Patent Number: 5,431,159
[45] Date of Patent: Jul. 11, 1995

[54] PULSE OXIMETRY

[75] Inventors: William Baker, Indianapolis; James C. Stevens, Mooresville, both of Ind.

[73] Assignee: Sentinel Monitoring, Inc., Indianapolis, Ind.

[21] Appl. No.: 732,332

[22] Filed: Jun. 17, 1991

Related U.S. Application Data

[63] Continuation of Ser. No. 190,661, May 5, 1988, abandoned.

[51] Int. Cl.$^6$ .............................................. A61B 5/00
[52] U.S. Cl. ........................................ 128/633; 356/41
[58] Field of Search ........................... 356/41, 39, 42; 128/633, 666

[56] References Cited

U.S. PATENT DOCUMENTS

| | | | |
|---|---|---|---|
| 3,638,640 | 2/1972 | Shaw | 356/41 |
| 3,847,483 | 11/1974 | Shaw et al. | 356/41 |
| 4,086,915 | 5/1978 | Kofsky | 128/633 |
| 4,266,554 | 5/1981 | Hamaguri | 128/633 |
| 4,356,448 | 10/1982 | Brogardh et al. | 250/231.1 |
| 4,407,290 | 10/1983 | Wilber | 128/633 |
| 4,653,498 | 3/1987 | New et al. | 128/633 |
| 4,714,080 | 12/1987 | Edgar et al. | 128/633 |
| 4,759,369 | 7/1988 | Taylor | 128/666 |
| 4,802,486 | 3/1989 | Goodman et al. | 128/633 |
| 4,807,630 | 2/1989 | Malinouskas | 356/41 |
| 4,807,631 | 3/1989 | Hersh et al. | 128/666 |
| 4,819,646 | 4/1989 | Cheung et al. | 128/666 |
| 4,834,532 | 5/1989 | Yount | 128/633 |
| 4,846,183 | 7/1989 | Martin | 356/41 |

FOREIGN PATENT DOCUMENTS 0128387 10/1975 Japan ..................... 128/633

OTHER PUBLICATIONS

Yee et al. "A Proposed Miniature Red/Infrared Oximetry . . . "; IEEE Trans. Biomed. Eng. vol. 24, pp. 195–197, Mar. 1977.
Schibli et al. "An Electronic for Red/Infrared Oximeters"; IEEE Trans. Biomed. Eng. vol. BME-25, No. 1, pp. 94–96, Jan. 1978.
Krishnan "Development of a Hybrid-Tip Oximeter . . . "; Master of Science Thesis in El. Eng., University of Washington, 1973.
Huch et al. "Limitations of Pulse Oximetry", The Lancet, Feb. 13, 1988, pp. 357, 358.
Nijboer et al. "Photoelectric Plethysmography Some Fundamental Aspects . . . "; Clin. Phys. Physial, Mar. 1981, vol. 2, No. 3, pp. 205–215.
Mendelson "Theory Development of Transcutaneous Reflectance Oximeter System . . . Ph.D. thesis", Case Western Resver University, May 25, 1983, pp. i–xxii, 1–254.
Rolfe (Ed.), "Noninvasive Physiological Measurements", vol. 1, Chapter 6, pp. 125–151, Challouer Plethipmorphay . . . Academic Press, New York, N.Y. 10003; 1979.
Mendelson "Noninvasive Transcutaneous Monitor of Antiviral Blood Gases"; IEEE Trans. on Biomed. Eng., vol. BME-31, No. 12, Dec. 1984, pp. 792–800.

Primary Examiner—Vincent P. McGraw
Attorney, Agent, or Firm—Cumpston & Shaw

[57] ABSTRACT

Non-invasive oximetry wherein red and infrared light from light sources energized at different frequencies is applied to arterial blood-containing tissue of a living subject. The red and infrared light coming from this tissue is sensed in order to obtain frequency-muliplexed information as to the absorption of said light by said tissue, the information being processed in order to derive therefrom a measure of percent oxygen saturation of said blood. The processing includes filtering for separating information represented by red light absorption from information represented by infrared light absorption. In particular, both notch and bandpass filters are used, and AM detectors provide for further separating such information into DC and AC components.

5 Claims, 4 Drawing Sheets

PULSE OXIMETRY

This is a continuation of application Ser. No. 07/190,661 filed on May 5, 1988, abandoned.

BACKGROUND OF THE INVENTION

1. Field of the Invention

This invention relates to non-invasive oximetry of the pulse type in which light, which has irradiated a volume of arterial blood within a subject, is sensed in order to determine oxygen saturation of the subject's blood. The light which contacts the subject, depending on its spectral content, is variously absorbed, reflected, scattered and transmitted by the blood and other tissue of the subject, before detection. The intensity and the change of intensity of either the reflected, scattered, or the transmitted light are used to determine oxygen saturation of the subject's blood. Such change is essentially due to the arterial pulse, which causes the volume of irradiated blood to vary in accordance with the arterial pulse.

2. Statement of the Prior Art

U.S. Pat. No. 3,847,483, issued Nov. 12, 1974 to Shaw et al, describes and claims an invasive oximetry method and apparatus wherein blood optical density is determined from measures of reflected intensity of red and infrared light transmitted to and from the blood. Both time and frequency multiplexing are used to separate red intensity from infrared intensity.

U.S. Pat. No. 4,086,915, issued May 2, 1978 to Kofsky et al, describes and claims a non-invasive oximetry method and apparatus wherein change of blood optical density, due to the arterial pulse, is determined from measures of change in transmitted or reflected intensity of red and infrared light incident on ear or other blood-perfused tissue of a living subject. Time multiplexing is used for separating change in red intensity from change in infrared intensity.

In the same vein are Hamaguri U.S. Pat. No. 4,266,554, May 12, 1981; Wilber U.S. Pat. No. 4,407,290, Oct. 4, 1983; New et al U.S. Pat. No. 4,653,498, Mar. 31, 1987; Edgar et al, U.S. Pat. No. 4,714,080, Dec. 22, 1987; and Aoyagi et al, laid-open Japanese Patent Application No. Sho 50/1975-128387. These disclose various circuit realizations and oximetric mathematical exegeses differing in detail from those which Kofsky, et al, supra apply to non-invasive, pulse oximetry.

Again, frequency multiplexing in oximetry is referred to in Yee et al, "A Proposed Miniature Red/Infrared Oximeter Suitable for Mounting on a Catheter Tip", IEEE Trans. Biomed. Eng., Vol. 24, pp. 195–197, March, 1977, who describe invasive and non-invasive oximetric probes, and, as well, Schibli et al, "An Electronic Circuit for Red/Infrared Oximeters", IEEE Trans. Biomed Eng., Vol. BME-25, No. 1, pp. 94–96, January, 1978, describe in vitro oximetry wherein blood optical density is determined from measures of reflected intensity of red and infrared light transmitted to and from extracorporeal blood using a probe of Yee et al, supra. V. M. Krishnan, in a Jun. 6, 1973 thesis for the Master of Science degree in Electrical Engineering, University of Washington, describes details of circuitry relating to frequency multiplexing, which Yee et al include by reference in their paper.

Lastly, Huch et al "LIMITATIONS OF PULSE OXIMETRY", The Lancet, Feb. 13, 1988, pp. 357, 358, presents one recent view of the character of results obtained by current pulse oximetric methods and apparatus.

It is the main object of the present invention to provide an oximeter wherein oxygen saturation measurement is based on non-invasively obtained, frequency-multiplexed, arterial-pulse modulated information contained in red and infrared radiation from blood-perfused tissue.

A particular object of the invention is to provide such oximeter wherein the red and infrared information is obtained from red and infrared light reflected from and scattered in the blood-perfused tissue.

SUMMARY OF THE PRESENT INVENTION

In the present invention, light from red and infrared sources irradiates a portion of a subject's finger, earlobe, or other blood-perfused tissue, and a photosensor senses such of said light as is returned from said portion, and produces therefrom a corresponding electrical signal. The sources are energized by pulse trains of differing, fixed frequencies, but constant in amplitudes, so that the light therefrom is also in two components, each having a different spectral content, and each varying in amplitude at a different frequency. The spectral content of the red component is chosen so that the absorption thereof by oxygenated blood is different from the absorption thereof by deoxygenated blood. The spectral content of the infrared component is chosen so that absorption thereof by oxygenated blood is about the same as for deoxygenated blood. However, the subject's arterial pulse varies the volume of blood in the irradiated portion of tissue, and thereby amplitude modulates each light component in accordance with the arterial pulse induced variations of blood volume in the tissue. Accordingly, the electrical signal produced by the photosensor also has two components. One component's amplitude varies at the frequency of energization of the red light source, and is proportional to absorption of the red light by the tissue. The other component's amplitude varies at the frequency of energization of the infrared light source, and is also proportional to absorption of the infrared light by the tissue.

The photosensor's electrical signal is processed by electrical circuitry which separates AC components thereof in accordance with the frequency of energization of said sources, and removes any out of band component which may be present in the photosensor's electrical signal.

In other words, all the information of interest contained in the radiation from the blood-perfused tissue has been frequency-multiplexed, so to speak, so that it is carried by a single signal, in a single channel, until the signal reaches a point where one desires to extract from it information which is at a single, or more accurately, in a narrow band of frequencies. In the present invention, when such point is reached by the frequency-multiplexed signal from the photosensor, the above said two components are obtained simultaneously, i.e., demultiplexed, by means of filter circuitry.

Further processing includes detecting the amplitude modulation of the AC components and measuring it, and using the resulting measures in computing percent oxygen saturation of the blood in the irradiated tissue.

DESCRIPTION OF PREFERRED EMBODIMENT

Figure 1:
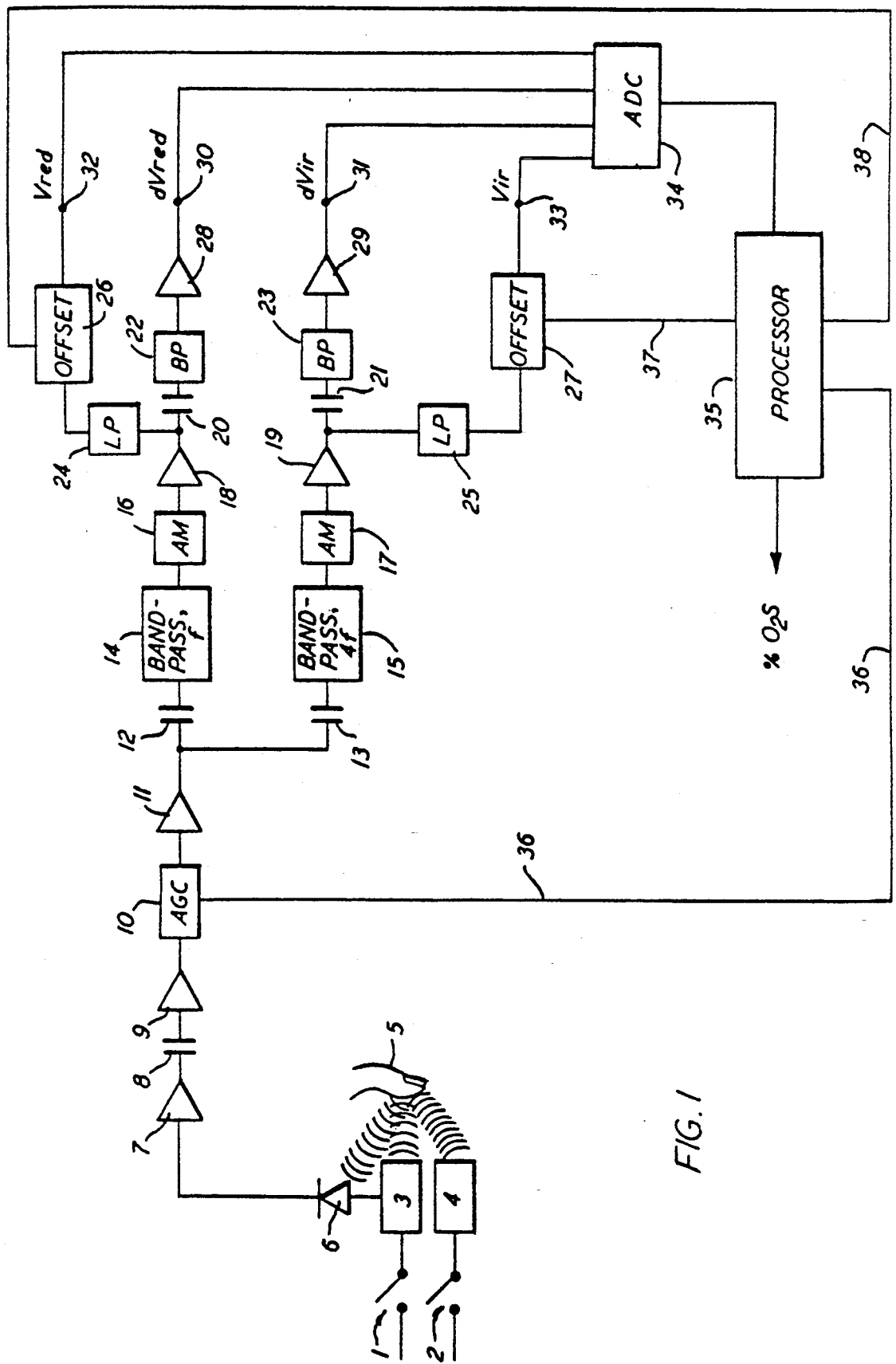
FIG. 1 is a box diagram of the invention.

In FIG. 1, switches 1 and 2 intermittently connect red LED 3 and infrared LED 4, respectively, to a source of electricity (not shown). Switch 1 makes and breaks at the frequency of $4f$, whereas switch 2 makes and breaks at the frequency f, where f is a frequency roughly an order of magnitude or more larger than about 60 Hz. The light of the LEDs irradiates a portion of a living subject's finger 5, and a photodiode 6 senses such of that light as is returned from said portion, an amplifier 7 being provided for producing an output voltage proportional to the current through said diode which current in turn is proportional to the radiation it receives from finger 5.

The voltage output of amplifier 7 is coupled by a capacitor 8 to a voltage amplifier 9, which in turn is coupled via an automatic gain control 10 to a voltage amplifier 11. The output voltage of amplifier 11 is coupled via capacitors 12 and 13 to respective filters 14 and 15.

Filter 14 passes a narrow band of frequencies containing frequency f whereas filter 15 passes a narrow band of frequencies containing frequency $4f$. Filters 14 and 15 are connected to respective AM detectors 16 and 17, which remove the carriers. Detector 16 produces a slowly varying voltage which contains information as to the effect on the red light of the irradiated portion of finger 5, whereas detector 17 produces a slowly varying voltage which contains information as to the effect on the infrared light of the irradiated portion of finger 5. Substantially all other information originally contained in the output voltage of amplifier 7 has been processed out by the circuitry coupled to amplifier 7 via capacitor 8. Thus, capacitor 8 eliminates DC or slowly-varying components, whereas the filters 14 and 15 eliminate any signal outside their respective f and $4f$ bands.

As is known in the prior art, the light picked up by photodiode 6 is a measure of the optical density of the tissue from which it comes, with respect to the spectral content of the red and infrared light irradiating such tissue. Hence, the output voltages of the AM detectors 16 and 17 are measures of red and infrared optical density, respectively. These voltages, after amplification by voltage amplifiers 18 and 19, are coupled by capacitors 20 and 21, respectively, to bandpass filters 22 and 23 the output voltages of which are amplified by voltage amplifiers 28 and 29, whose output voltages appear at terminals 30 and 31 respectively. The AM detector output voltages are also directly coupled via low pass filters 24 and 25, respectively, to offsets 26 and 27, which have voltage output terminals 32 and 33, respectively.

Despite the presence of filters 22 through 25, offsets 26 and 27, and amplifiers 28 and 29, in FIG. 1 the voltages dVred, dVir, Vred, and Vir at output terminals 30 through 33 represent, respectively, change of red optical density of the blood in the irradiated portion of tissue, change of infrared optical density thereof, red optical density thereof, and infrared optical density thereof.

The terminals 30 through 33 are connected to an analog to digital converter (ADC) 34 in order to convert the analog voltages at those terminals to digital signals which it applies to a microprocessor 35, and which are suitable for processing by microprocessor 35, which last, as indicated by connection lines 36, 37, and 38, also controls AGC 10 and offsets 26 and 27. Microprocessor 35 examines the magnitudes of the signals it receives from ADC 34 and adjusts AGC 10 as necessary to keep the analog signals at terminals 30 through 33 within a range appropriate to the capabilities of ADC 10. Similarly, the offsets 26 and 27 are caused by microprocessor 35 to set the levels of the DC signals at terminals 30 and 33. Ultimately, the signal processing by the microprocessor produces a number representing percent oxygen saturation, which number will be displayed, recorded or otherwise rendered in a form perceptible to medical or other personnel.

Figure 2A:
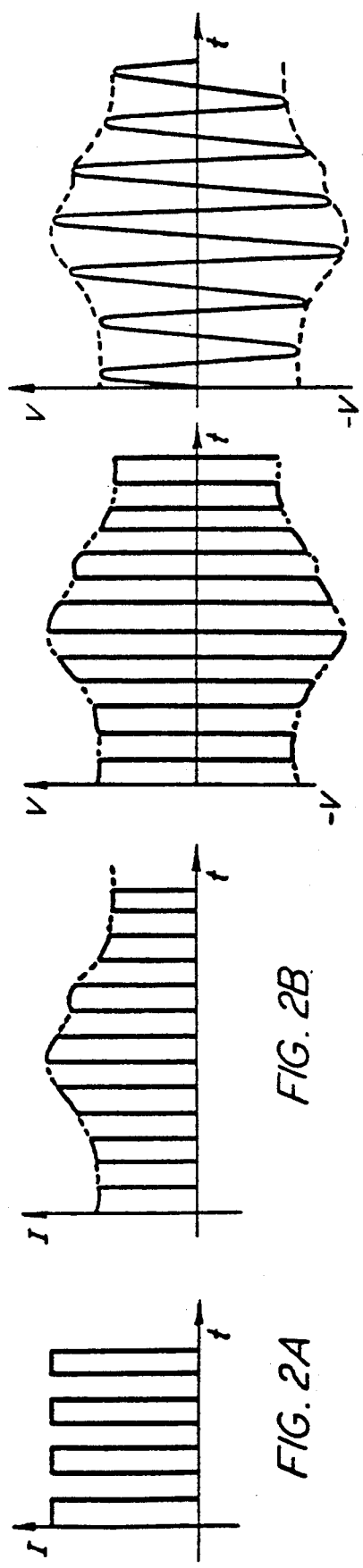
FIGS. 2A through 2G show the signal waveforms found in the invention considered in the light of FIG. 1.

FIGS. 2A, B, C, D, E, F and G show the signal wave forms at various points in FIG. 1, beginning with either one of the LEDs 3 and 4. Taking the vertical as amplitude or intensity, and the horizontal as time, then at 2A the LED output is in the form of constant amplitude light pulses, due to pulses of current through the LED.

At 2B, the output of amplifier 7, the LED's light pulses, modulated by the tissue and blood of the subject, have been converted into DC voltage pulses whose envelope represents AC arterial blood pulses superimposed on a DC component which is due to blood and tissue, among other things. The pulse train of 2B next encounters capacitor coupling which removes DC component, so that the pulse train becomes a two-sided signal as shown in 2C, which represents modulation of an AC-only carrier.

The pulse trains in 2B, and 2C, of course, would be more complex than shown since there are two LEDs irradiating the finger, not one, so that the spectral content of the photodiode output contains both f and $4f$ pulse components. However, when the mixture of these components passes through the filters 14 and 15, the f and $4f$ information is separated from each other into two trains each like that shown in 2D, which is much like 2C, except for rounding of the heretofore squarish peaks, by the filters.

Next, the 2D pulse trains encounter the AM detectors 16 and 17, which remove the f and $4f$ carriers, and thereby produce 2E signals whose amplitudes represent the combined effect of blood, tissue and arterial pulse in the portion of finger irradiated by the red and infrared light pulses.

The 2E signals then provide signals 2F, as a result of passing through capacitors 20 and 21, and bandpass filters 22 and 23, and, simultaneously, signals 2G, as a result of passing through LP filters 24 and 25, and offsets 26 and 27.

The signals 2G vary little in amplitude since the arterial pulse component has been much attenuated (FIG. 2G exaggerates their variation), and so represent the respective effects of a fixed portion of blood and tissue on the red and infrared light irradiating those portions, whereas signal 2F represents the variation of those effects by the arterial pulse in said portion.

Signals 2F and 2G, of which there are, of course, two sets of each type, namely, a first set of 2F and 2G signals corresponding to the red light, and a second set of 2F and 2G signals corresponding to the infrared light, provide information which may be used, for example only, for obtaining the approximate derivatives utilized for determining percent oxygen saturation by Kofsky et al, supra, in conjunction with various coefficients (which may be, but need not necessarily be the pseudo coefficients of Kofsky et al).

Figure 2B:
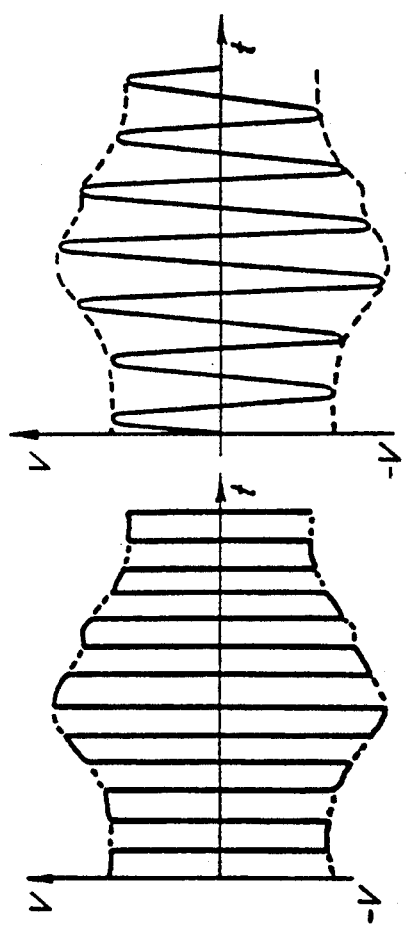
Figure 2C:
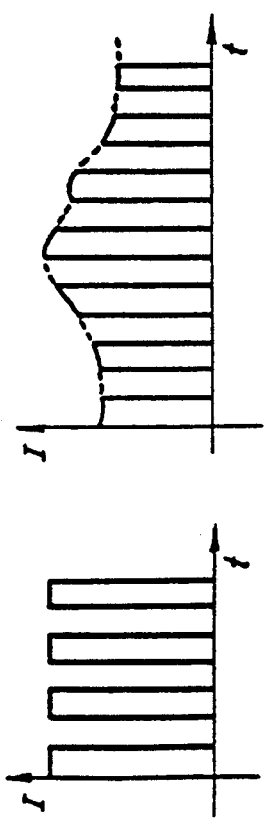
Figure 2D:
Figure 2E:
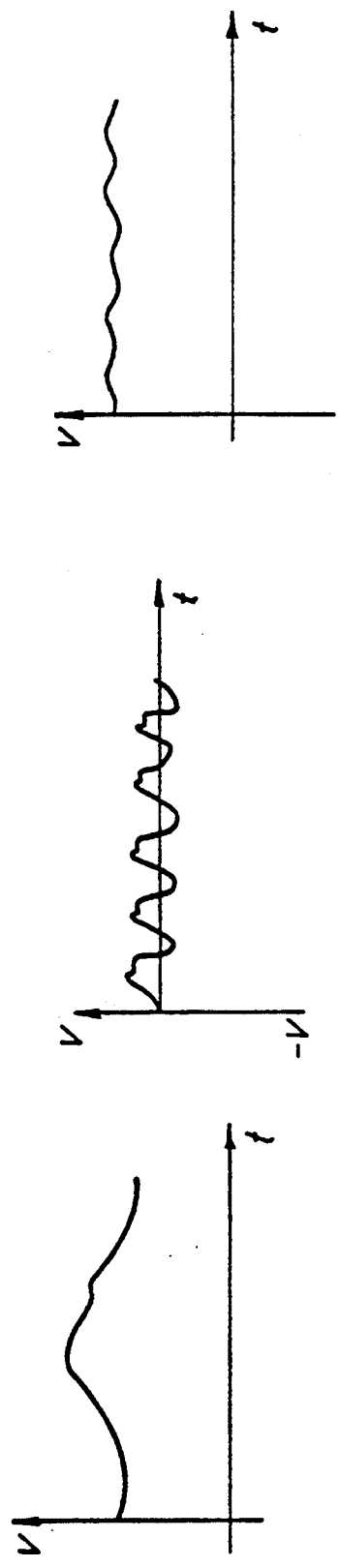
Figure 2F:
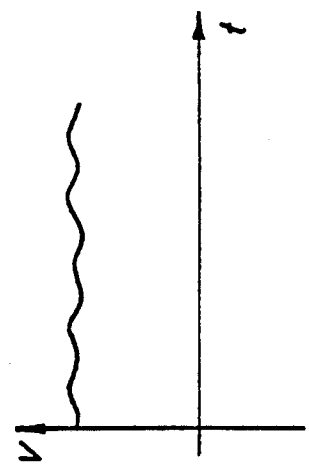
Figure 2G:
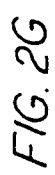
Figures 3, 3A:
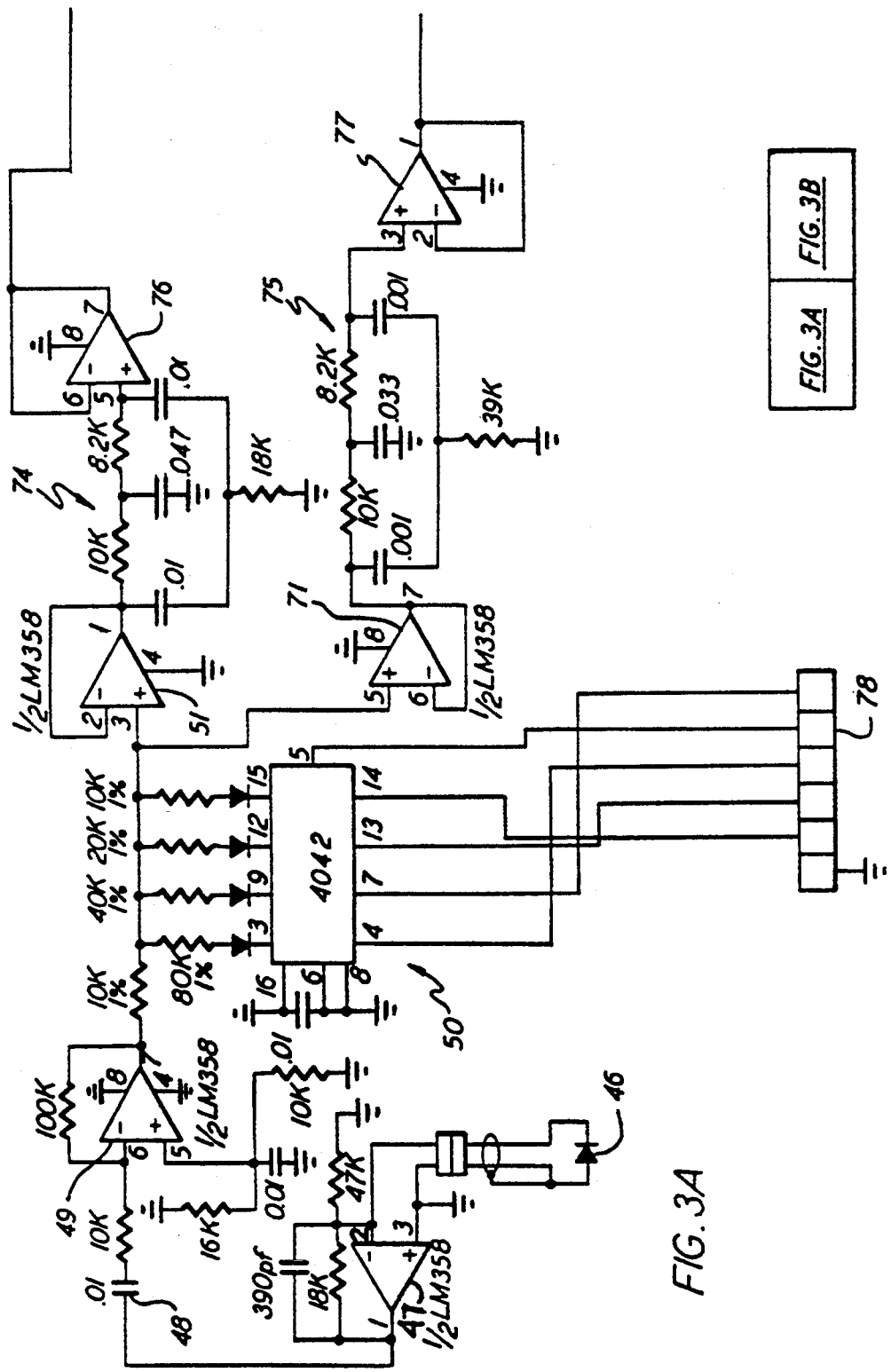
FIGS. 3A and 3B show a detailed circuit schematic of an actual embodiment of the invention, FIG. 3 indicating the orientation of FIGS. 3A and 3B with respect to one another.
Figure 3B:
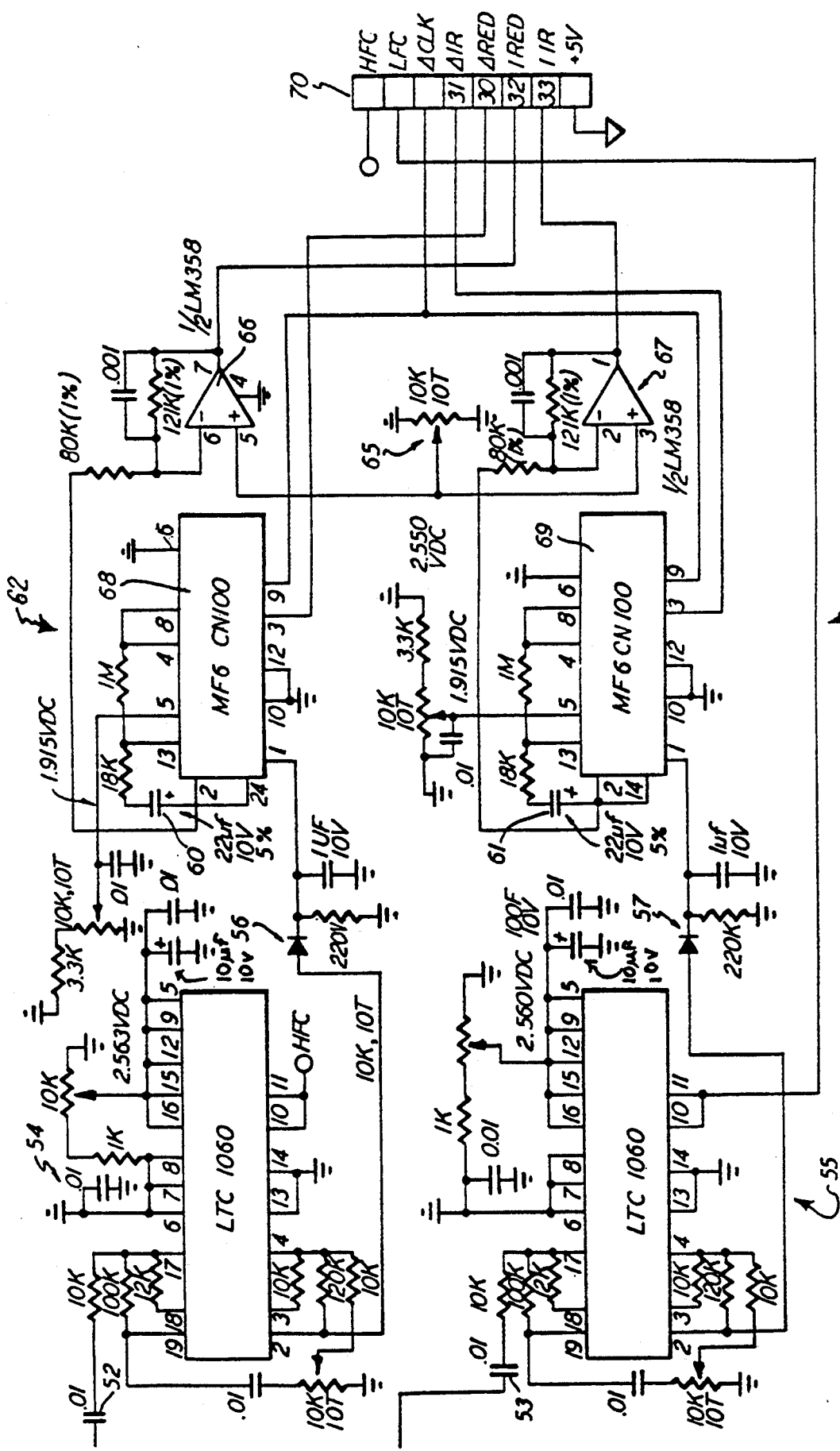

Turning to FIGS. 3, 3A and 3B, and beginning with FIG. 3A, a photodiode 46, corresponding to diode 6 of FIG. 1, is illuminated by red and infrared light from perfused tissue of an earlobe, finger, or the like, irradiated by LEDs (not shown in FIG. 3, but such as 3 and 4 of FIG. 1, and pulse energized as disclosed in connection therewith). The photodiode current which is a mixture of two sets of pulses, as shown in FIG. 2B, and at frequencies f and $4f$, is amplified by amplifier 47 whose output voltage is coupled via capacitor 48 to amplifier 49, of which the output traverses a resistive voltage divider 50, corresponding to AGC 10.

Amplifier 47 is fitted out as a voltage amplifier which converts the photodiode current to voltage at a higher signal level by means of the illustrated circuitry which will be recognized as conventional by one of ordinary skill in the art, and so will not be described further herein. Similarly, the remaining amplifiers 49, 51, 71, 76, 77, 66 and 67 are amplifiers fitted out as voltage amplifiers by the illustrated circuitry of conventional design. For the most part, the amplifiers serve to maintain adequate signal levels and/or buffering, as is conventional. In FIG. 1, which is very much idealized, bandpass filters 14 and 15 would function ideally, that is, filter 14 would stop all frequencies but f and filter 15 would stop all frequencies but $4f$. In actual fact, however, as shown in FIG. 3A, the input voltage to amplifier 51 is applied also to an amplifier 71. The output voltages of amplifiers 51 and 71 in turn are applied to passive notch filters 74 and 75 which notch out, respectively, a narrow band of frequencies including $4f$, and a narrow band of frequencies including f. Ideally, all frequencies but $4f$ would get to filter 54, and all frequencies but f would get to filter 55. The filters 74 and 75 connect to capacitors 52 and 53 via respective voltage amplifiers 76 and 77 which make up for the voltage attenuation due to the filters 74 and 75, which are typical third order passive RC filters.

Capacitors 52 and 53 correspond to FIG. 1's capacitors 12 and 13, and like them, couple the red and infrared components of signal voltage to active bandpass filters 54 and 55 and to the counterparts of FIG. 1's LP filters 24 and 25. The latter filters are provided by circuitry (not shown) internal to the chips 68 and 69, to which the detector output voltages are connected via capacitors 60 and 61 (each with series resistor), corresponding to capacitors 20 and 21, FIG. 1. These capacitors with series resistor stop very low frequencies, so that these, with the two chips, provide bandpass filters 62 and 63.

The offset amplifiers 66 and 67 are shown to be conventional differential amplifiers each receiving on one input terminal an AM detector output voltage, but on the other terminal the same offset voltage which may be established either automatically (as by a processor, corresponding to the processor 35 in FIG. 1), or as in FIG. 3B, by manually setting a resistive potentiometer 65 to provide the same predetermined portion of the system supply voltage to each of the offset amplifiers' said other terminals.

As shown in FIG. 3B, the terminals 30 through 33 are provided by a connector 70, which also provides, as indicated by the labels for other connector terminals, system supply voltage (+5 v.), high frequency control (HFC), low frequency control (LFC), and a clock voltage CLK, typically a fraction of a megaHz frequency of a clock in, say, a processor corresponding to the processor 35.

As shown in FIG. 3B, each of filters 54 and 55 is constituted by a commercially available LTC 1060 chip, each of which is a switched capacitor bandpass filter, and is fitted out with the illustrated circuitry, which is of conventional nature, calculated to make the filter pass a narrow band of frequencies, in the one case centered on the frequency f, and in the other, $4f$.

Each of AM detectors 56 and 57, which correspond to detector 16 and 17, FIG. 1, is a conventional half-wave rectifier whose DC output voltage is smoothed by an RC filter before passing to pins 1 of the switched capacitor bandpass filters 62 and 63 provided by commercially available MF6 CN100 chips 68 or 69, and capacitors 60 and 61. A buffer amplifier (not shown) inside each chip presents the detected voltage on each chip pin 2 for applying it to an offset amplifiers 66 or 67.

The HFC terminal of the connector 70 proper is shown as connecting to an unmarked terminal external to connector 70. The chip of filter 54, in turn has a similar external terminal marked HFC, connected to its pins 10 and 11. This is merely for drafting convenience, and symbolizes an interconnecting line between those pins and terminal HFC of the connector. An actual connection is shown between the LFC terminal and the pins 10 and 11 of filter 55's chip.

The CLK signal, which may come from a processor corresponding to the processor 35, connects to pins 9 of chips 68 and 69, whereby to provide for setting filter center frequencies.

In the circuit of FIG. 3, f is 1.1 kHz and $4f$ is 4.4 kHz. The spectral content of ambient light, power line effects, etc., is well below these frequencies, and is largely filtered out by the high pass filter effect due to the circuitry of amplifier 49. After this, the composite signal applied to amplifiers 51 and 71 consists essentially of a band of frequencies including f and a band of frequencies including $4f$, each band being substantially free of undesired spectral components. The frequencies within the pass bands, and on either side of the center frequencies, are the so-called side-band frequencies. The f and $4f$ bands do overlap enough that elimination of the overlapping spectral components in the bandpass filters 54 and 55 would demand more stringent frequency selectivity of filters 54 and 55 than is desirable from some design points of view. The notch filters 74 and 75 minimize the need for excessive bandpass filter selectivity simply by removing f and $4f$ bands before the respective $4f$ and f signals are applied to respective filters 55 and 54.

The bandpass filters provided by the internal low pass filter of the MF6 CN100's and external capacitors 60 and 61 with their series resistors, function not only to remove the DC component of the AM detector outputs, namely, Vred and Vir, but also stabilize the remaining AC components corresponding to dVred and dVir, by removing detector noise. In this case, the bandpass is (0.1–10)Hz. This filtering is done to avoid jitter. Thus, if the AC components are subjected by the processor to detection of peaks as represented by the voltage swings at terminals 30 and 31, jitter may look like peaks to the microprocessor.

Insofar as the DC components are concerned, it will be noted that the offset amplifiers 66 and 67 are fitted out as low pass elements which attenuate the arterial pulse components of the AM detector outputs.

The radiation picked up by the photosensor 46 (or 6, FIG. 1) is that which is returned from an area of skin contacting the receptive surface of the photosensor. The returning radiation is what remains after the radiation emitted by the LED's interacts with the corneal, epidermal and dermal layers, and is commonly thought to be a measure of how much of the incident radiation has been absorbed by the hemoglobin, regardless of whether it is being "returned" as a result of having been scattered from the erythrocytes, or is being "returned" as a result of having been transmitted through the tissue. In other words, it is an empirical fact that the desired measured value, namely, how much radiation has been absorbed by the hemoglobin can be measured by measuring either how much radiation is scattered from the blood, or how much gets through the blood, and this is why substantially the same circuitry can be used for both reflective and transmissive optoplethysmographic $SaO_2$ determination.

Ideally, the red and infrared radiation would be isobestic with respect to all the components of tissue with which they interact, except with respect to oxygenation of the hemoglobin. However, this is not the case, so the ultimate (for the two wave length case) empirical expression relating to the degree of oxygenation to the four voltages at terminals 31 through 33 is:

$$SaO2 = (A+R)/(B+CR). \quad (1)$$

In equation (1), A, B and C are constants, whereas R is approximately (I'red/Ired)/(I'ir/Iir), wherein I represents original intensity, and I' the time derivative of original intensity with Vred, Vir, dVred and dVir being practical measures of intensities and intensity time derivatives (that is, the peak to peak values of the dVs, i.e., dVred and dVir, are usable as a measure of derivatives, namely, I'red and I'ir).

The foregoing is in accordance with the teachings of Kofsky et al, supra, wherein it is taught the time derivative of a medium's optical density D for a given wavelength is a fraction of the time derivative of optical path length in the medium, concentrations of various components of the medium, and attenuation coefficients of such components, so that, supposing that:

$$D' = I'/I, \quad (2)$$

then measurements of the voltages at terminals 30 through 33, for known values of $SaO_2$, can be used as a basis for determining suitable values for A, B and C in Equation (1), or for constants in some other empirically-determined expression for $SaO_2$.

Were ideal isobestic conditions to obtain, equation (1) would reduce to (A'+B'R), essentially the same thing except that C is eliminated, i.e., A' is A/B and B' is 1/B.

Kofsky et al, supra, teach evaluating four attenuation coefficients of a system of equations involving Vred, Vir, dVred and dVir. In the practice of the present invention, equation (1) represents a linear approximation to the Kofsky et al approach. In the present invention, we use a 880 nanometer LED for the infrared wavelength. This wavelength is close enough to being isobestic that using the isobestic form of equation (1) in the practice of our invention provides satisfactory accuracy. For respectively brief and lengthy studies of optoplethysmography as applied to measurement of hemoglobin oxygenation, see J. A. Nijboer et al, "Photoelectric Plethysmography-Some Fundamental Aspects of the Reflection and Transmission Method", *Clin. Phys. Physiol. Meas.*, 1981, Vol. 2, No. 3, pp 205–215, and Y. Mendelson, "Theory And Development Of A Transcutaneous Reflectance Oximeter System For Noninvasive Measurements Of Arterial Oxygen Saturation", pp i-xxii, and 1-254. The Mendelson item is a Ph. D. thesis submitted to Case Western Reserve University, May 25, 1983, and is available from University Microfilms International, 300 N. Zeeb Road, Ann Arbor, Mich. 48106.

Finally, see also Rolfe (Ed.), Non-Invasive Physiological Measurements, Vol, 1, Academic Press Inc., 111 Fifth Avenue, New York, N.Y. 10003; 1979, Chapter 6, pp. 125–151, Photoelectric Plethysmography For Estimating Cutaneous Blood Flow (A. V. J. Challoner).

The LED's 3 and 4 were 660 nm and 880 nm, respectively, the former being operated at 40 ma peak current, and with a 33% duty cycle and 76 mw peak electrical power. The LED 4 was operated at 6 ma peak current, and with a 50% duty cycle and 7.2 mw peak electrical power. The photosensor 46 (or 6, FIG. 1) was a PIN photodiode, wired to the amplifier 47 (or 7, FIG. 1) by twisted pair in grounded external shield cabling, in order to avoid noise pick-up (e.g. RF), a desideratum which can also be fulfilled by a fiber optic link conducting light from the finger to photosensor 46 (or 6, FIG. 1) which can be close coupled to amplifier 47 (or 7, FIG. 1) so as to make it easier to avoid noise pick-up.

The circuit of FIGS. 3A, and 3B, is shown as using the reflective mode to pick-up returning finger radiation. However, it may also be used with a transmission type pick-up, i.e., where the sensor 46 (or 6, FIG. 1) is located on the other side of the finger, earlobe, or the like, from the LED's.

While the mode or modes of light/tissue interaction are rather complex (see Nijboer et al, above-cited, for example), it appears that the teachings of Kofsky et al are equally applicable to reflective and transmissive LED/photosensor pick-ups, hence only empirical parameters (mainly gains and calibration constants) might vary from those given in FIGS. 3A and 3B.

The circuit values, tolerances, voltage levels, etc., of the FIG. 3A/3B circuit, being shown thereon, nothing need be said here about these. However, it is to be noted that except for electrolytics (which have polarity indicated) the capacitors are either Mylar or ceramic, (the feedback capacitor of amplifier 47 is NPO), and their values are in microfarad units. The chips were as follows:

LM358: generic
4042; generic
LTC 1060: Linear Technology
MF6 CN100: National Semiconductor The contact between LEDs, photosensor and tissue should be a light-tight as possible, yet exert approximately no deforming pressure on the t issue.

The FIG. 1 LED-photosensor-finger arrangement is roughly that of an actual example of the invention. However, in practice, the LED's are as close together as possible, so that, as FIG. 1 suggests, their illumination patterns overlap considerably. However, the photosensor has a 10.08 $mm^2$ effective sensing area whose center line, at the skin surface, is about 0.4 in. from the center of the LED-illuminated patch of skin surface. Being supported in a probe surface having a curvature which will fit the average finger without significantly deforming its soft tissue, the angle between the effective direction of LED illumination of finger 5, and the effective direction of radiation from the finger to the photosensor is about 56°. As compared to LED-to-photosensor lesser or greater spacings, the 0.4 in. spacing gives optimum signal to noise ratio of the photodiode current.

In the foregoing, we have described our invention in great detail. Such detail is subject to modification. All the prior art references cited herein, we hereby incorporate herein, in toto, by reference, and commend them, and their like, insofar as applicable, to those skilled in the art, for further elaboration of the art of oximetry, as now known.

We claim:

1. An optoplethysmographic oximeter having means for causing radiation absorbed by tissue of a living being to provide frequency-multiplexed first and second signals;

said first signal being a measure of oxygenation of a volume of arterial blood in said tissue, and of said volume;

said second signal being a measure of said volume;

said second signal not being a measure of said oxygenation, as compared to said first signal:

said oximeter also having demultiplexing means for demultiplexing said signals, whereby to provide for using said signals to compute a measure of percent oxygen saturation of said blood;

said demultiplexing means including first and second notch filter means each being effectively connected to the first said means for having said first and second signals applied simultaneously thereto, said first notch filter means being responsive to filter said first and second signals such as to produce a third signal which includes said first signal but not said second signal, and said second notch filter means being responsive to said first and second signals such as to produce a fourth signal which includes said second signal but not said first signal;

said oximeter having means for applying said radiation to said tissue, and means for sensing such of said radiation as comes from said tissue.

2. The oximeter of claim 1 wherein said demultiplexing means includes first and second band pass filter means connected respectively to said first and second notch filter means for receiving therefrom, respectively and simultaneously, said third and fourth signals, and first band pass filter means being responsive to said third signal for producing a fifth signal corresponding substantially only to said third signal, and said second band pass filter means being responsive to said fourth signal for producing a sixth signal corresponding substantially only to said fourth signal.

3. The oximeter of claim 2 wherein said fifth and sixth signals are amplitude modulated carrier signals differing in frequency, and there being first and second detector means connected to said first and second band pass filter means respectively, for receiving therefrom, respectively and simultaneously, said fifth and sixth signals;

said first detector means being responsive to said fifth signal for producing therefrom a seventh signal which varies in amplitude at a rate in accordance with the pulse rate of said living being, said second detector means being responsive to said sixth signal for producing therefrom an eighth signal which varies in amplitude at a rate in accordance with said pulse rate, but one said amplitude being affected by the oxygen content of said blood, the other said amplitude being relatively unaffected by said oxygen content.

4. Apparatus for measuring oxygen saturation of the blood of a subject, said apparatus comprising:

(a) light source means and a light sensor means constructed and arranged for cooling light from said light source means to a volume of said blood via the tissue of said subject, and for simultaneously coupling said light sensor means via said tissue to light from said volume of blood;

(b) said light having first and second components periodically varying in intensity, the period of said first component being different from that of said second compartment, and said first component also having a spectral content different from the spectral content of said second component;

(c) said spectral contents being such that the tissue of said subject, the blood in said tissue, and changes of said volume of blood, will affect their intensities substantially alike, but also such that intensity of one said component's spectral content will be affected by the oxygen in the blood in said volume more than will be the intensity of the other said component's spectral content;

(d) said light sensor means being responsive to light coupled thereto, for producing a first signal of magnitude corresponding to the intensity of said light coupled thereto;

(e) signal processing means connected to said light sensor means for receiving therefrom said first signal and producing therefrom a second signal and a third signal, said second signal and said third signal being produced simultaneously, said second signal being substantially free of spectral content of the said second component, and said third signal being substantially free of spectral content of the said first component, said second and third signals each having a frequency and amplitude corresponding respectively to the frequency of the subject's arterial pulse and to the oxygen content of the blood in said volume;

(f) first and second AM detecting means connected to said signal processing means for detecting the amplitudes of said second and third signals respectively and simultaneously;

(g) and means for producing, from each of said second and third signals, an additional pair of signals, one of which represents the corresponding one of the last said amplitudes, and the other of which represents the pulsatile component thereof;

said signal processing means of paragraph (e) including a pair of notch filters and a pair of bandpass filters;

one said notch filter being connected to receive said first signal for producing a notch-filtered signal free of spectral content of one said component, and the other said notch filter being connected to said first signal for producing a notch-filtered signal free of spectral content of the other said component;

said signal processing means also including a pair of bandpass filters, one said bandpass filter being connected to receive the first said notch filter's signal for producing a bandpass filter signal containing only spectral content of said other said component, and the other said bandpass filter being connected to receive the second said notch filtered signal for producing a bandpass filtered signal containing only spectral content of said one said component;

whereby said bandpass filtered signals provide said second and third signals.

5. An oximeter comprising:
(a) a source of red light and means for energizing it at a first fixed frequency, and a source of infrared light and means for energizing it at a second fixed frequency, said second frequency being different from said first frequency;
(b) there being means for coupling the light of said sources to a portion of a living subject's tissue, perfused with arterial blood varying in volume in accordance with the said subject's arterial pulse, whereby the intensity of said light becomes varied as a function of the optical properties of said portion of tissue and the blood therein;
(c) the said red light and the said infrared light being unequally absorbed by oxygenated hemoglobin, and said red light and said infrared light being substantially equally absorbed by deoxygenated hemoglobin;
(d) light sensor means and means for coupling infrared and red light from said portion of tissue, as aforesaid, to light sensor means for producing an electrical signal having component at said first frequency, and a second component at said second frequency; and
(e) processing means responsive solely to said electrical signal's components for producing a signal whose amplitude represents percent oxygen saturation of the blood in said portion of tissue;

said processing means including a first notch filter and a first bandpass filter, said first notch filter receiving said electrical signal for providing a first notch-filtered signal free of said second frequency component, said first bandpass filter receiving said first notch filtered signal for producing therefrom a first signal representing only said first frequency component;

said processing means also including a second notch filter and a second bandpass filter, said second notch filter receiving said electrical signal for providing a second notch-filtered signal free of said first frequency component, said second bandpass filter receiving said second notch filtered signal for producing therefrom a second signal representing only said second frequency component.

* * * * *